United States Patent [19]
Rand

[11] Patent Number: 5,386,445
[45] Date of Patent: Jan. 31, 1995

[54] METHOD AND APPARATUS FOR ELECTRON BEAM FOCUSING ADJUSTMENT BY ELECTROSTATIC CONTROL OF THE DISTRIBUTION OF BEAM-GENERATED POSITIVE IONS IN A SCANNING ELECTRON BEAM COMPUTED TOMOGRAPHY SCANNER

[75] Inventor: Roy E. Rand, Palo Alto, Calif.
[73] Assignee: Imatron, Inc., San Francisco, Calif.
[21] Appl. No.: 166,545
[22] Filed: Dec. 14, 1993
[51] Int. Cl.$^6$ ............................................. H01J 35/06
[52] U.S. Cl. ......................................... 378/10; 378/4; 378/138
[58] Field of Search ............... 378/4, 10, 12, 13, 113, 378/137, 138; 250/396 ML, 396 R, 492.3

[56]        References Cited
             U.S. PATENT DOCUMENTS

| 4,122,346 | 10/1978 | Enge | 378/10 X |
|---|---|---|---|
| 4,158,142 | 6/1979 | Haimson | 378/10 |
| 4,392,235 | 7/1983 | Houston | 378/10 |
| 4,521,900 | 6/1983 | Rand | 378/137 |
| 4,521,901 | 6/1983 | Rand | 378/138 |
| 4,669,102 | 5/1987 | Puumalainen | 378/10 |
| 4,736,396 | 4/1988 | Boyd et al. | 378/4 |
| 4,914,681 | 4/1990 | Klingenbeck et al. | 378/12 |
| 5,172,401 | 12/1992 | Asari et al. | 378/10 |
| 5,193,105 | 3/1993 | Rand et al. | 378/138 X |

*Primary Examiner*—David P. Porta
*Attorney, Agent, or Firm*—Flehr, Hohbach, Test, Albritton & Herbert

[57] ABSTRACT

In a scanning electron beam CT system, the electron beam is focused by controlling the distribution of beam-generated ions electrostatically. The upstream (self-expanding, de-focusing) beam region and downstream (converging, self-focusing) beam region are distinguished by the absence or presence of beam-generated positive ions. The relative lengths of these two beam regions are electrostatically controlled such that beam de-focusing in the upstream region compensates for beam self-focusing in the downstream region. In this fashion, essentially zero external focusing strength is required, and the magnetic focus coil used in the prior art is eliminated. Located downstream from the electron gun, a positive ion electrode ("PIE") determines the position of the boundary between the two regions, and thus the relative length of each region. The PIE is a disk-like electrode, mounted coaxially to the beam optic axis within the drift tube, and coupled to a large positive potential. Varying the PIE potential varies the inter-region boundary position, and thus the relative magnitudes of the beam de-focusing and self-focusing effects. A PIE focus potential is determined by varying the potential while examining the output of electron beam monitors with an oscilloscope. Further, by dynamically varying the PIE potential, the present invention adjusts electron beam focusing, even during a scan. Positive ions are removed from the upstream region by a periodic ion clearing electrode ("PICE") whose high rate of change of axial potential creates alternating axial fields that rapidly sweep away ions.

15 Claims, 4 Drawing Sheets

METHOD AND APPARATUS FOR ELECTRON BEAM FOCUSING ADJUSTMENT BY ELECTROSTATIC CONTROL OF THE DISTRIBUTION OF BEAM-GENERATED POSITIVE IONS IN A SCANNING ELECTRON BEAM COMPUTED TOMOGRAPHY SCANNER

FIELD OF THE INVENTION

The present invention relates generally to scanning electron beam computed tomographic X-ray systems, and more particularly to focusing and adjusting the focus of the electron beam in such systems without using magnetic or electrostatic lenses.

BACKGROUND OF THE INVENTION

Scanning electron beam computed tomography ("CT") systems are described generally in U.S. Pat. Nos. 4,352,021 to Boyd, et al. (Sep. 28, 1982), and 4,521,900 (Jun. 4, 1985), 4,521,901 (Jun. 4, 1985), 4,625,150 (Nov. 25, 1986), 4,644,168 (Feb. 17, 1987), and 5,193,105 (Mar. 9, 1993), all to Rand, et. al. Applicant refers to and incorporates herein by reference each above listed patent to Rand, et al.

As described in the above-referenced patents, an electron beam is produced by an electron gun at the upstream end of an evacuated generally conical shaped housing chamber. A large electron gun potential (e.g., 130 kV) accelerates the electron beam downstream along the chamber axis, and further downstream, a beam optical system focuses and deflects the beam to scan along an X-ray producing target. It is understood that the final beam spot on the target is much smaller than the original beam size upon exiting the electron gun.

The beam optical system includes a magnetic focus coil, quadrupole coils, and deflection coils. The X-rays penetrate an object (e.g., a patient) and are detected by a detector array 22. The detector array 22 and targets 14 are coaxial with, and define planes orthogonal to, the system axis of symmetry 28. The output from the detector array is digitized, stored, and computer processed to produce a reconstructed X-ray video image of a portion of the object.

In the chamber region upstream of the beam optical system, a diverging beam is desired. In the upstream region, the electron beam can advantageously self-expand due to its own space-charge. The self-expansion depends on the force created by the electron space-charge. By contrast, downstream from the beam optical system, a converging, self-focusing, beam is desired.

The vacuum chamber contains residual or introduced gas that ionizes in the presence of the electron beam, producing positive ions. While these positive ions are useful in the downstream chamber region where a converging beam is desired, in the upstream region they can detrimentally counteract the desired beam expansion. Unless removed by an external electrostatic field upstream, the positive ions become trapped in the negative electron beam, neutralizing the space-charge needed for the desired beam self-expansion. In fact, neutralization can destabilize and even collapse the beam.

The usual arrangement in prior art scanning electron beam scanners is to remove such positive ions by passing the electron beam axially through at least one ion clearing electrode ("ICE") located in the upstream region. The ICE is coupled to an electrode potential of about 1 kV, and creates a transverse electric field. The transverse field sweeps away the slowly moving positive ions, without disturbing the considerably faster moving electrons, which have been accelerated by some 130 kV.

In this manner, ICE's remove positive ions only from the upstream region, permitting positive ions to accumulate downstream from the beam optics system. Downstream, positive ions beneficially neutralize beam space-charge, which permits the beam's attractive magnetic field to converge and self-focus the beam. Thus, downstream, convergence depends on the magnetic field created by the electrons in the electron beam.

The result is a self-repulsive, de-focusing beam in the upstream region, and a self-focusing beam in the downstream region. Elements of the beam optical system then focus and fine tune the converged beam as it scans along the X-ray target, to produce a sharp reconstructed X-ray image.

The upstream and downstream chamber regions are segregated by a washer-shaped positive ion electrode ("PIE"), coupled to a high positive potential, e.g., 2 kV. The PIE creates a large axial field that prevents positive ions (formed downstream) from migrating upstream, where their presence would be detrimental. Near the intersection of the upstream and downstream regions, there is usually placed a magnetic solenoid focus coil that provides and fine tunes the beam focus in response to a varying coil current.

While magnetic solenoid focus coils are used in the prior art, it is advantageous to reduce the number of components, including such coils, in a scanning electron beam CT system.

In a scanning electron beam CT system, there is a need for a mechanism that can focus the electron beam, and for a means for adjusting such mechanism, that obviates the need for a magnetic solenoid focus coil. Further, there is a need for an electron beam focus mechanism that permits dynamic focus fine tuning during a scan.

The present invention discloses such a mechanism.

SUMMARY OF THE INVENTION

The present invention focuses an electron beam in a scanning electron beam CT system by electrostatically controlling the distribution of beam-generated ions. The relative lengths of the upstream (self-expanding, defocusing) and downstream (converging, self-focusing) beam regions are electrostatically controlled such that beam de-focusing in the upstream region compensates for beam self-focusing in the downstream region. If the relative lengths of the two regions are properly chosen, essentially zero external focusing strength is required, and the magnetic focus coil used in the prior art is eliminated.

Located downstream from the electron gun, a positive ion electrode ("PIE") determines the position of the boundary between the two regions, and thus the relative length of each region. The PIE is a disk-like electrode, mounted coaxially to the beam optic axis within the drift tube portion of housing 10, and coupled to a large positive potential. The resultant axial field prevents positive ions from migrating past the PIE, upstream toward the electron gun. Varying the PIE potential varies the inter-region boundary position, and thus the relative magnitudes of the beam de-focusing and self-focusing effects. The required PIE potential is determined by varying the potential while examining the output of appropriate electron beam monitors.

Further, by dynamically varying the PIE potential, the present invention adjusts electron beam focusing, even during a scan.

In the preferred configuration, the drift tube region separating the electron gun from the PIE is too narrow to accommodate a conventional ICE without modifying the drift tube. Therefore, positive ions are removed from this upstream region by a periodic ion clearing electrode ("PICE"). A PICE comprises several spaced-apart washer-like electrodes coaxial to the beam optic axis, with alternate PICE electrodes coupled, respectively, to large and small potentials. The resultant high rate of change of axial potential creates alternating axial fields that rapidly sweep away ions. Alternative designs with conventional, e.g., transverse field, ICE's are also possible.

Other features and advantages of the invention will appear from the following description in which the preferred embodiments have been set forth in detail in conjunction with the accompanying drawings.

DESCRIPTION OF THE PREFERRED EMBODIMENTS

Figure 1:
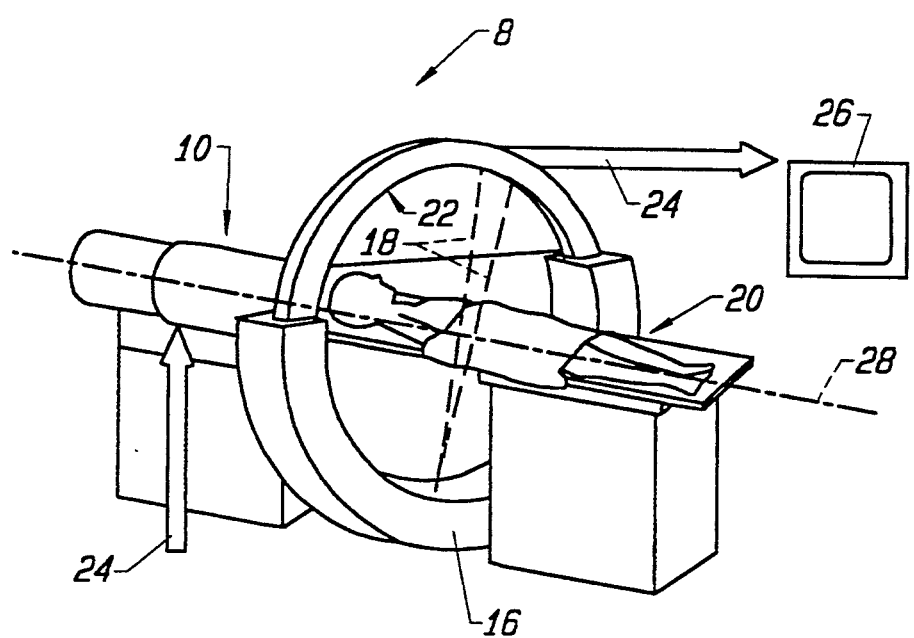
FIG. 1 depicts a generalized scanning electron beam computed tomography X-ray system, including electron beam focusing according to the present invention.
Figure 2:
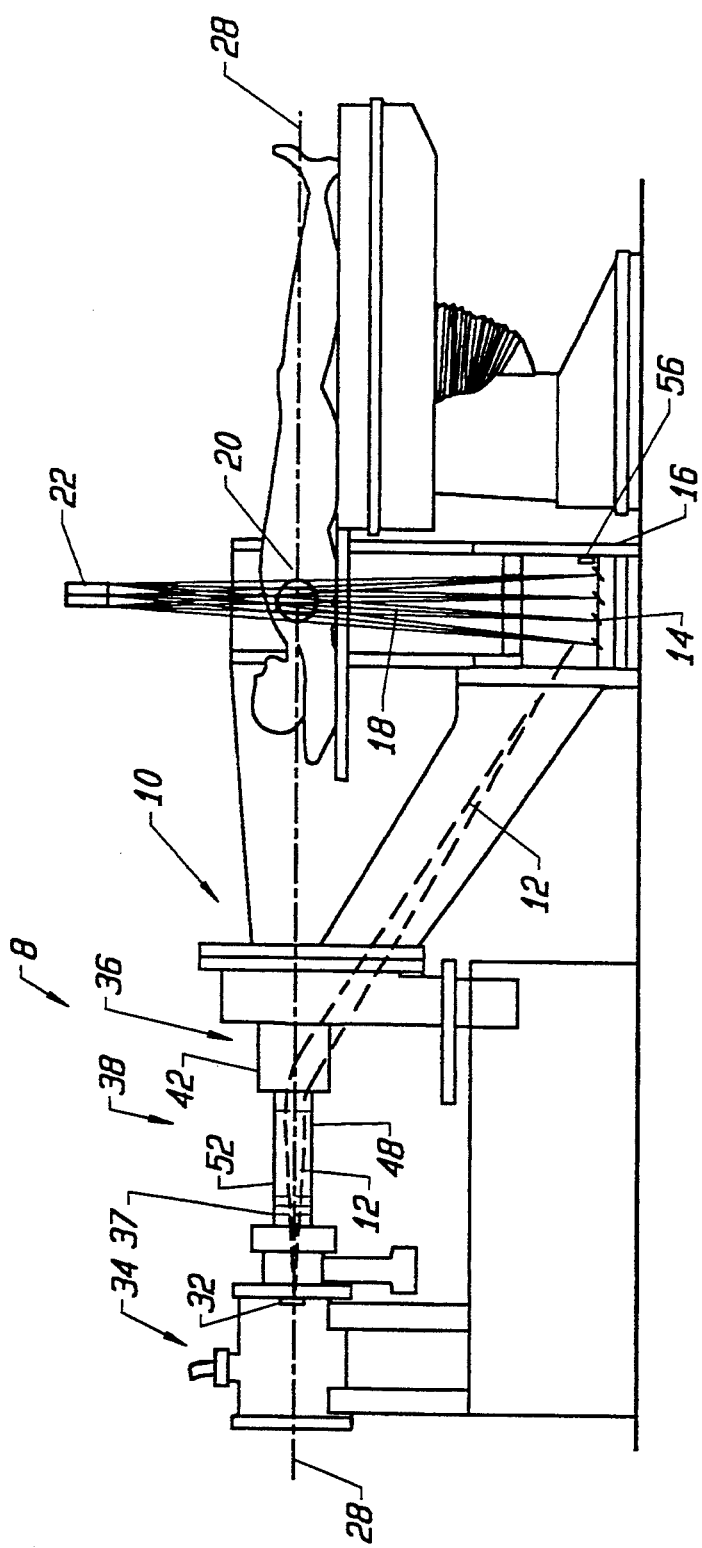
FIG. 2 is a longitudinal view of the system shown in FIG. 1.

As shown in FIG. 1 and FIG. 2, a generalized scanning electron beam CT X-ray system 8 includes a vacuum chamber housing 10 wherein an electron beam 12 is generated by an electron gun 32 located in upstream region 34, in response to high excitation (e.g., 130 kV). The electron beam is then caused by optical system 38 to scan at least one circular target 14 located within front lower portion 16 of chamber 12.

When scanned by the focused electron beam, the target emits a moving fan-like beam of X-rays 18. X-rays 18 then pass through a region of a subject 20 (e.g., a patient or other object) and register upon a detector array 22 located diametrically opposite. The detector array outputs data to a computer processing system (indicated by arrows 24) that processes and records the data, producing an image of a slice of the subject on a video monitor 26. As indicated by the second arrow 24, the computer processing system also controls the system 8 and the electron beam production therein.

As described earlier, gases in housing 10 produce positive ions in the presence of the electron beam 12. While positive ions are beneficial in the downstream, self-focusing region 36, they must be removed (or at least be suitably controlled) in the upstream, self-expanding defocusing region 34.

According to the present invention, beam optical system 38 includes a PIE 48, a PICE 52, deflecting coils and quadrupole coils, collectively coils 42. Coils 42 contribute a focusing effect, which is used to help shape the beam spot as it scans one of the targets 14. It is to be noted that beam optical system 38, in contrast to the prior art, does not include a magnetic focus coil.

Figure 3:
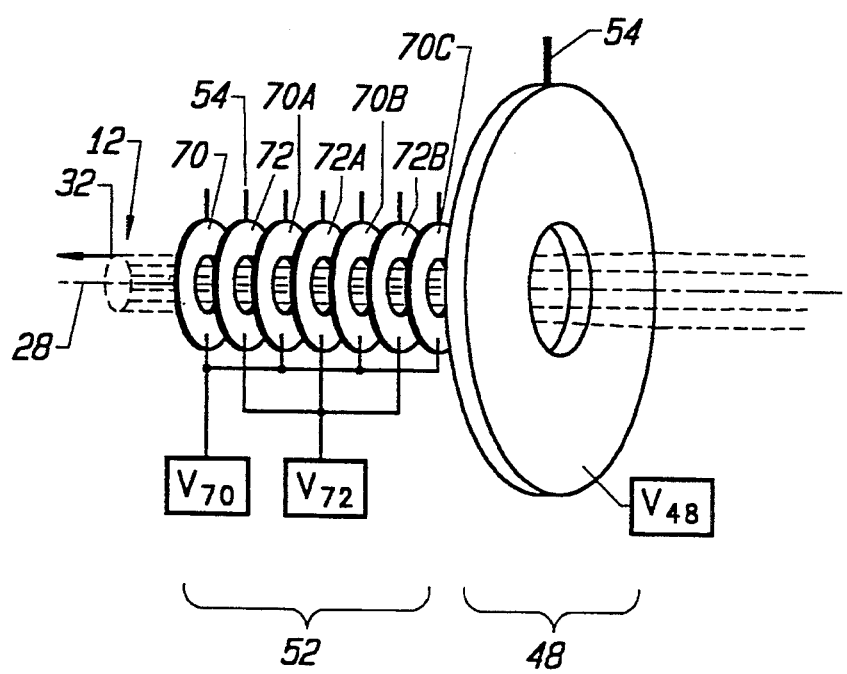
FIG. 3 is a perspective view of the PICE-PIE portion of the beam optical assembly 38, according to the present invention.

As shown in FIGS. 2 and 3, PIE 48 and PICE 52 are mounted within housing 10 between the electron gun 32 and coils 42 such that the electron beam 12 passes axially through the PICE and PIE coaxially along the system axis of symmetry 28.

With reference to FIG. 3, PIE 48 is preferably a planar washer whose center opening is at least as large as the electron beam diameter at that region, typically about 2 cm. PIE 48 is preferably coupled to a large positive potential (e.g., +2 kV) $V_{48}$. The PIE is made from a relatively inert conducting material that does not outgas within chamber 10, e.g., stainless steel or copper. The PIE is mounted within chamber 10 using one or more posts 54 made from an insulating material such as ceramic.

Figure 4A:
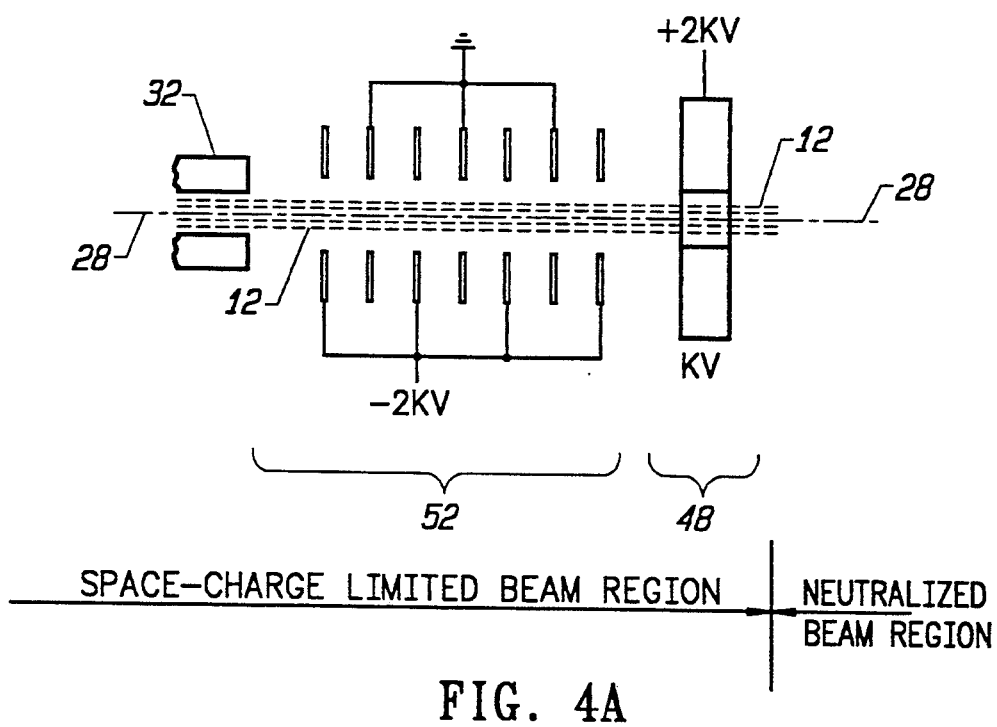
FIG. 4A is a longitudinal cross-sectional view of the PICE-PIE portion of the beam optical assembly 38 depicted in FIG. 3.
Figure 4B:
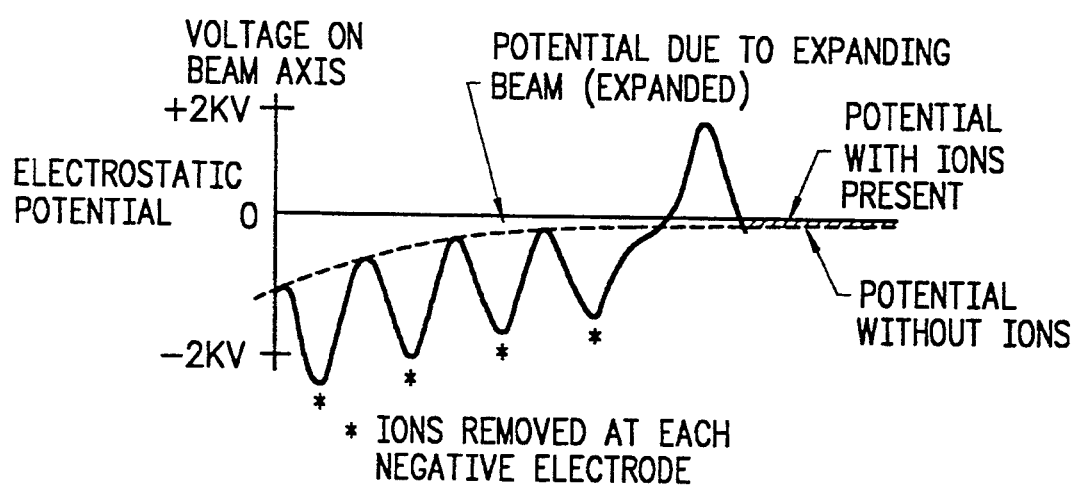
FIG. 4B depicts electrostatic potential at various longitudinal positions for the PICE-PIE depicted in FIG. 3.
Figure 4C:
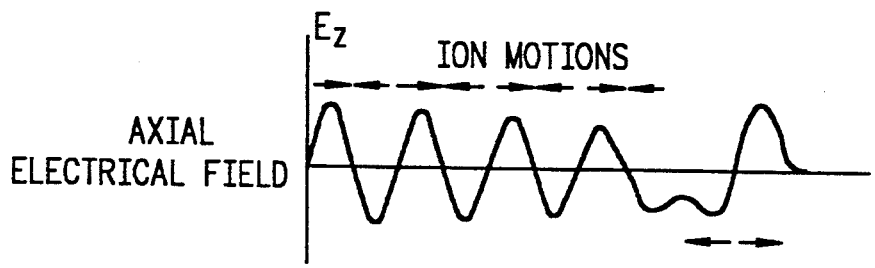
FIG. 4C depicts axial electric field at various longitudinal positions for the PICE-PIE depicted in FIG. 3.

The PIE produces an axial field that prevents positive ions from migrating upstream toward PICE 52 (see FIG. 4C). Such upstream migration would be detrimental and would interfere with the production of a sharply self-focused beam spot at the X-ray target. According to the present invention, PIE 48 further serves to sharply define the interface between the upstream region and the downstream region.

In prior art scanning electron beam CT system such as that disclosed in U.S. Pat. No. 5,193,105, the drift tube was sufficiently wide to permit using at least one ICE upstream of a PIE, to remove positive ions in the upstream, beam expanding region. However, in the present invention, the drift tube is narrowed in diameter to about 3.8 cm, too small a dimension to accommodate an ICE.

Therefore, in place of an ICE, the present invention removes positive ions from the upstream region 34 using a PICE 52, disposed adjacent electron gun 32 and upstream from PIE 48. PICE 52 preferably comprises a plurality of disk-like elements 70, 72 spaced apart coaxially along the axis 28. The PICE elements preferably stainless steel or a similar relatively inert conducting material that does not outgas within chamber 10. Insulating posts 54 are used to mount PICE 52 within the drift chamber 10.

Alternate PICE electrodes, e.g., 70, 70A, 70B, 70C are together coupled to a first potential source $V_{70}$, and the intermediate electrodes, e.g., 72, 72A, 72B are together coupled to a second potential source $V_{72}$. In the preferred embodiment of FIG. 3, seven PICE disks are used, $V_{70} \approx -2$ kV and $V_{72} \approx 0$ V (e.g., ground), although other potentials could be used, including possibly +2 kV and ground. A design consideration for the PICE is that within a relatively short lateral distance, e.g., about 5 cm, a sufficiently high rate of change of axial potential must be created to rapidly remove ions. The $V_{70}$, $V_{72}$ potentials are sufficient in magnitude to create the desired field but, in comparison with the 130 kV electron gun potential, are not sufficient to disturb the electron beam flow.

Further, PICE 52 advantageously subjects the electron beam 12 to an electric field notwithstanding discontinuities in housing 10 that create gaps, such as 37, over which a conventional ICE could not be used (assuming space permitted such use).

With reference to FIG. 3, it is understood that upstream from PIE 48 (e.g., to the left of PIE 48), positive electrons are removed by PICE 52, and the electron beam 12 expands, or de-focuses, due to space-charge of the electrons within the beam. The magnitude of the defocusing force at various points along axis 28 will vary with the beam diameter and space-charge density.

According to the present invention, PIE 48 separates the upstream region (e.g., the beam expanding or defocusing region) from the downstream region (e.g., the beam converging or self-focusing region). Because positive ions exist downstream from PIE 48 (e.g., to the right in FIG. 3), the electron space-charge is neutralized and the beam will converge or self-focus toward axis 28 due to the beam's self-magnetic field. The magnitude of the self-focusing force will vary along axis 28 as a function of the beam diameter and current density, which produces the self-magnetic field.

According to the present invention, between the upstream and downstream regions, there will be an axial location for which the beam expanding effect in the entire upstream region compensates the beam converging effect in the entire downstream region. Then essentially zero external focusing force will be required to focus the scanning electron beam on to a target 14.

By varying the PIE potential $V_{48}$, the boundary between the ion-free region and the neutralized region can be moved. In this manner, the relative length of the two regions can be varied until an upstream region length and a downstream region length result, for which the beam converging and diverging effects compensate one another.

Preferably the magnitude of PIE $V_{48}$ required for compensation is determined by varying $V_{48}$ while observing the output from beam monitoring devices 56 (see FIG. 2) on an oscilloscope. The optimum value of $V_{48}$ will be used. The use of "W"-wire devices 56 for monitoring beam quality in a scanning electron beam CT system is described in U.S. Pat. No. 4,631,741 (1986) to Rand, et al. Because the use of beam monitoring devices is known in the art, further description is not presented here.

Within system 8, stray electric and magnetic fields, and inexact dimensions of chamber 10 can vary ion distribution within the beam, and require fine tuning of the electron beam focus. This fine tuning is also provided by varying PIE potential $V_{48}$, which potential may be varied to control the focus dynamically during a scan. For example, an appropriate $V_{48}$ may be a DC voltage level about which a varying AC voltage is superimposed. If desired, the shape of the AC voltage can be suitably keyed by computer mechanism 24 to compensate for stray fields and inexactness in chamber 10 dimensions, as a function of beam scan position along an X-ray target 16.

It will be appreciated that although the PIE-PICE combination may constitute an electrostatic lens, this lens is weak and negative, contributing little to the overall focusing effect. The focusing effect of such a lens is significantly less than that of the beam self-forces, which are controlled by the beam ion distribution, which in turn is controlled by the PIE potential, according to the present invention.

The present embodiment varies both the strength of the effective electrostatic lens and the beam ion distribution as a function of the PIE potential. However, since the electrostatic lens strength and ion distribution are actually separate effects, a suitable electrode arrangement would permit focusing by maintaining the electrostatic focus effect constant or zero, while varying the beam magnetic self-forces by means of the ion distribution.

FIG. 4A depicts the PICE-PIE assembly 52-48 in longitudinal cross-section, showing the role of PIE 48 in demarking the interface between the upstream space-charge limited, de-focusing beam region, and the downstream neutralized, self-focusing beam region. FIG. 4B depicts the electrostatic potentials measurable at various locations along axis 28. FIG. 4C depicts the electric fields along Z-axis 28, resulting from the PICE and PIE units, and also shows the motions of the ions.

In summary, in contrast to the use of a magnetic focus coil in the prior art, the present invention configures a PIE unit to provide the necessary focusing and dynamic focusing. Further, the PICE-PIE configuration used in the present invention requires less drift tube space, consumes less power, and operates more reliably than a prior art magnetic focus coil.

Modifications and variations may be made to the disclosed embodiments without departing from the subject and spirit of the invention as defined by the following claims. For example, although a focus mechanism has been described for use in a scanning electron beam CT system, such mechanism could be used in other applications as well, e.g., high current electron accelerator injectors, and possibly electron beam welders.

What is claimed is:

1. A mechanism for focusing an electron beam generated in a vacuum housing chamber having an upstream defocusing region wherein a first force due to electron space-charge expands and de-focuses the electron beam, and having a downstream focusing region wherein a second force due to neutralization of said space-charge and due to said electron beam's self-magnetic field converges the electron beam, the electron beam travelling in a downstream direction defining a beam axis, the mechanism comprising:

a positive ion electrode, disposed downstream from a generator of said electron beam substantially coaxially with said electron beam, said electrode being coupled to a positive potential that creates an axial field controlling any upstream migration through said electrode of positive ions formed downstream;

said positive potential determining an axial boundary location separating said upstream and downstream regions, for which location effects of said first force and said second force are substantially equal;

wherein essentially zero external focus force is required to focus said electron beam.

2. The mechanism of claim 1, wherein said positive ion clearing electrode is a planar disk having a central opening sized to permit passage of said electron beam therethrough.

3. The mechanism of claim 1, wherein said positive potential is varied during a scan of said electron beam;

said varied potential altering ion distribution in said electron beam to dynamically focus said electron beam during said scan.

4. The mechanism of claim 1, wherein said positive potential has a magnitude of approximately +2 kV.

5. A system for focusing an electron beam generated in a vacuum housing chamber having an upstream defocusing region wherein a first force due to electron space-charge expands and de-focuses the electron beam, and having a downstream focusing region wherein a second force due to neutralization of said space-charge and due to said electron beam's self-magnetic field converges the electron beam, the electron beam travelling in a downstream direction defining a beam axis, the mechanism comprising:

first means, disposed in said upstream region coaxially with said beam axis, for removing positive ions from said upstream region such that electron space-charge produces said first force causing electron beam divergence in said upstream region;

second means, disposed downstream from said first means coaxially with said beam axis, for controlling any upstream migration through said second means of positive ions formed downstream and for determining an axial boundary location separating said upstream and downstream regions;

wherein said axial boundary location is such that effects of said first force and said second force are substantially equal such that essentially zero external focus force is required to focus said electron beam.

6. The system of claim 5, wherein said first means creates alternating axial fields for rapidly sweeping away ions.

7. The system of claim 6, wherein said first means includes a periodic ion clearing electrode comprising:

a plurality of planar disk elements, each defining a central opening sized to permit passage of said beam therethrough, spaced-apart and disposed coaxial with said beam axis and upstream from said second means;

wherein alternate ones of said planar disk elements are coupled to first and second sources of potential, such that a potential difference between said first and second sources of potential creates said alternating axial field between adjacent ones of said planar disks.

8. The system of claim 5, wherein said second means includes an electrode coupled to a source of positive potential that creates an axial field controlling any upstream migration through said electrode of positive ions formed downstream.

9. The system of claim 8, wherein said source of positive potential is varied during a scan of said electron beam;

said varied potential altering ion distribution in said electron beam to dynamically focus said electron beam during said scan.

10. A scanning electron beam CT X-ray system, including:

means for generating an electron beam within a vacuum housing chamber having an upstream de-focusing region wherein a first force due to electron space-charge expands the electron beam, and having a downstream de-focusing region wherein a second force due to neutralization of said space-charge and due to said electron beam's self-magnetic field converges said electron beam, said electron beam travelling in a downstream direction defining a beam axis;

means for scanning said electron beam along an X-ray emitting target;

a positive potential electrode, disposed downstream from said means for generating substantially coaxial with said electron beam, said electrode being coupled to a positive potential that creates an axial field controlling any upstream migration through said electrode of positive ions formed downstream;

said positive potential determining an axial boundary location separating said upstream and downstream region, for which location effects of said first force and said second force are substantially equal;

wherein essentially zero external focus force is required to focus said electron beam upon said X-ray emitting target.

11. A method for focusing an electron beam generated in a vacuum housing chamber having an upstream defocusing region wherein a first force due to electron space-charge expands and de-focuses the electron beam, and having a downstream focusing region wherein a second force due to neutralization of said space-charge and due to said electron beam's self-magnetic field converges the electron beam, the electron beam travelling in a downstream direction defining a beam axis, the method including the step of:

creating an axial field controlling any upstream migration of positive ions formed downstream such that an axial boundary location separating said upstream and downstream regions exists within said chamber, for which position effects of said first force and said second force are substantially equal;

wherein essentially zero external focus force is required to focus said electron beam.

12. The method of claim 11, wherein said step of creating an axial field includes:

disposing a positive potential electrode downstream and coaxial with a source generating said electron beam, disposed downstream from the electron gun substantially coaxially with said electron beam; and coupling said electrode to a source of positive potential creating said axial field.

13. The method of claim 12, wherein:

said step of disposing includes disposing a planar disk having a central opening sized to permit passage of said electron beam therethrough; and wherein said step of coupling includes coupling said electrode to a source of potential of approximately +2kV magnitude.

14. The method of claim 11, wherein said axial field is varied during a scan of said electron beam, said varied axial field altering ion distribution in said electron beam to dynamically focus said electron beam during said scan.

15. The method of claim 12, wherein said axial field is varied during a scan of said electron beam by varying said source of potential, said varying potential altering ion distribution in said electron beam to dynamically focus said electron beam during said scan.

* * * * *